United States Patent [19]

Takahata et al.

[11] Patent Number: 5,175,160

[45] Date of Patent: Dec. 29, 1992

[54] ANTIMICROBIAL AGENT FOR ANIMALS

[75] Inventors: Toshihiro Takahata, Davis, Calif.; Masakazu Takei, Chiba; Masahiro Kato, Tokyo; Tadayoshi Miura, Kanagawa; Toshiyuki Yoshioka, Tokyo, all of Japan

[73] Assignee: Daiichi Pharmaceutical Co., Ltd., Tokyo, Japan

[21] Appl. No.: 747,416

[22] Filed: Aug. 19, 1991

Related U.S. Application Data

[63] Continuation of Ser. No. 391,034, Aug. 9, 1989, abandoned.

[30] Foreign Application Priority Data

Aug. 9, 1988 [JP] Japan .................. 63-198199

[51] Int. Cl.⁵ .................. A61K 31/395; C07D 265/34
[52] U.S. Cl. .................. 514/230.2; 544/101
[58] Field of Search .................. 544/101; 514/230.2

[56] References Cited

U.S. PATENT DOCUMENTS 4,382,892  5/1983  Hayakawa et al. .................. 544/101

FOREIGN PATENT DOCUMENTS

| | | |
|---|---|---|
| 57-46986 | 3/1982 | Japan . |
| 0203085 | 12/1982 | Japan .................. 544/101 |
| 0072589 | 4/1983 | Japan .................. 544/101 |
| 0116217 | 2/1984 | Japan .................. 544/101 |
| 59-116217 | 7/1984 | Japan . |
| 60184014 | 9/1985 | Japan . |
| 60-202822 | 10/1985 | Japan . |
| 62-145088 | 6/1987 | Japan . |
| 0047005 | 3/1982 | United Kingdom . |
| 0206283 | 12/1986 | United Kingdom . |

OTHER PUBLICATIONS

Chemical and Pharmaceutical Bulletin, vol. 32, No. 12, pp. 4907–4913, 1984, I. Hayakawa, et al.
"Synthesis Antibacterial Activities of Substituted 7-Oxo-2,3-Dihydro-7H-Pyrido (1,2,3-de)(1,4) Benzoxazine-6-. . . ".
Antimicrobial Agents & Chemotherapy, vol. 23, No. 3, pp. 509–551 (1983).
Antimicrobial Agents & Chemotherapy, vol. 31, No. 2, pp. 325–327 (1987).
Antimicrobial Agents & Chemotherapy, vol. 29, No. 1, pp. 163–164 (1983).

Primary Examiner—Johann Richter
Attorney, Agent, or Firm—Oblon, Spivak, McClelland, Maier & Neustadt

[57] ABSTRACT

An antimicrobial agent for animals is disclosed. The agent comprises as an effective component a racemate of a 3S-type compound of a pyrido[1,2,3-de][1,4]benzoxazine derivative represented by the formula (I):

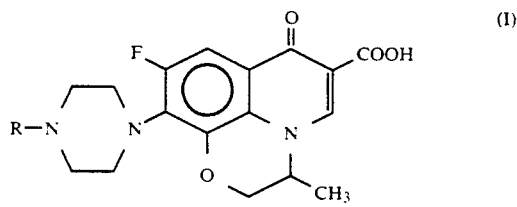

wherein R is a $C_{1-6}$ alkyl group, provided that R cannot be a methyl group when the pyrido[1,2,3-de][1,4]benzoxazine derivative is a racemate, or a salt or a hydrate thereof. The compounds possess a low toxicity, are safe antimicrobial agents for animals, have a broader antimicrobial spectrum, and are effective against various infectious diseases of animals.

2 Claims, No Drawings

ANTIMICROBIAL AGENT FOR ANIMALS

This application is a continuation of application Ser. No. 07/391,034, filed on Aug. 9, 1989, now abandoned.

BACKGROUND OF THE INVENTION

1. Field of the Invention

This invention relates to an antimicrobial agent for animals comprising as an effective component a racemate or a 3S-type compound of a pyrido[1,2,3-de][1,4-]benzoxazine derivative represented by the formula (I):

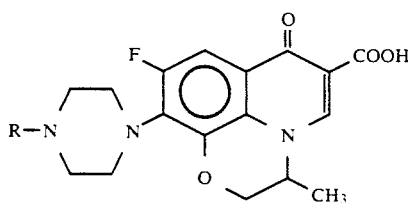

wherein R is a $C_{1-6}$ alkyl group (provided that R cannot be a methyl group when the pyrido[1,2,3-de][1,4]benzoxazine derivative is a racemate), or a salt or a hydrate thereof. The antimicrobial agent of this invention is useful for the prevention, cure, or treatment of various infectious diseases of animals.

2. Description of the Background

The increased number of livestock and poultry confined to a unit area by the current stockbreeding practices gives rise to the proliferation of various infectious diseases among farm animals and domestic fowl. Damage caused by such infectious diseases has been increasing yearly, posing an economic problem to the industry.

Conventionally, antibiotics such as tylosin, oxytetracycline, etc., and synthetic antimicrobial agents such as oxolinic acid, piromidic acid, etc. have been added to feed or water, orally administered, or injected to animals for the prevention and cure of their infectious diseases.

These conventional antimicrobial agents, however, have drawbacks such as insufficient antimicrobial activity, a narrow antimicrobial spectrum, development of microbial resistance to the agents, low disease-curing effect, inadequate safety, side effects, high production costs, and the like.

Among pyrido[1,2,3-de][1,4]benzoxazine derivatives of the above formula (I) a compound which is a racemate has been reported in Japanese Patent Laid-open No. 184014/1985. Japanese Patent Laid-open No. 116217/1984 discloses antimycoplasmal activity of ofloxacin. These compounds, however, possesses only a narrow antimicrobial spectrum, and their antimicrobial activity is not necessarily sufficient.

SUMMARY OF THE INVENTION

Accordingly, one object of the present invention is to provide a nontoxic and safe antimicrobial agent for animals having a broad antimicrobial spectrum.

It is another object of the present invention to priovide pharmaceutical compositions containing such antimicrobial agents.

It is another object of the present invention to provide a method for treating or preventing a disease in animals by administering such antimicrobial agents.

These and other objects, features and advantages of the present invention, which will hereinafter become more readily apparent from the following detailed description, have been achieved by the inventors' discovery that racemates and 3S-type compounds, in particular, of pyrido[1,2,3-de][1,4]benzoxazine derivatives represented by the formula (I):

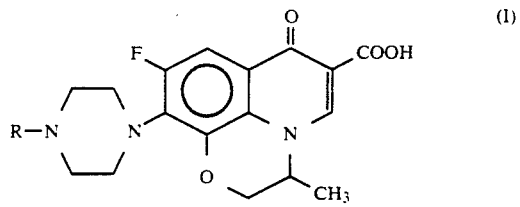

(wherein R is a $C_{1-6}$ alkyl group, provided that R cannot be a methyl group when the pyrido[1,2,3-de][1,4]benzoxazine derivative is a racemate) exhibit a superior preventive or curing effect against a wide variety of infectious diseases of animals with little or no toxicity.

DETAILED DESCRIPTION OF THE PREFERRED EMBODIMENTS

There are optical isomers of pyrido[1,2,3de][1,4]benzoxazine derivatives represented by formula (I) [such derivatives are hereinafter referred to as Compounds (I)]. Among these, racemates or 3S-type compounds are used for the antimicrobial agents for animals of this invention. The 3S-type compounds bodies possess higher antimicrobial activities and are thus especially preferred.

The following compounds are given as examples of formula (I) compounds used in this invention:

(1) 3S-9-fluoro-2,3-dihydro-3-methyl-10-(4-methyl-1-piperazinyl) -7-oxo-7H-pyrido[1,2,3-de][1,4]benzoxazine-6-carboxylic acid hemihydrate;

(2) 3(RS)-9-fluoro-2,3-dihydro-3-methyl-10-(4-ethyl-1-piperazinyl) -7-oxo-7H-pyrido[1,2,3-de][1,4]benzoxazine-6-carboxylic acid;

(3) 3(RS)-9-fluoro-2,3-dihydro-3-methyl-10-(4-n-propyl-1-piperazinyl) -7-oxo-7H-pyrido[1,2,3-de][1,4-]benzoxazine-6-carboxylic acid;

(4) 3(RS)-9-fluoro-2,3-dihydro-3-methyl-10-(4-iso-propyl-1-piperazinyl) -7-oxo-7H-pyrido[1,2,3-de][1,4-]benzoxazine-6-carboxylic acid;

(5) 3(RS)-9-fluoro-2,3-dihydro-3-methyl-10-(4-n-butyl-1-piperazinyl) -7-oxo-7H-pyrido[1,2,3-de][1,4]benzoxazine-6-carboxylic acid;

(6) 3S-9-fluoro-2,3-dihydro-3-methyl-10-(4-ethyl-1-piperazinyl) -7-oxo-7H-pyrido[1,2,3-de] [1,4]benzoxazine-6-carboxylic acid;

(7) 3S-9-fluoro-2,3-dihydro-3-methyl-10-(4-n-propyl-1-piperazinyl) -7-oxo-7H-pyrido[1,2,3-de][1,4]benzoxazine-6-carboxylic acid; and (8) 3(RS)-9-fluoro-2,3-dihydro-3-methyl-10-(4-ethyl-1-piperazinyl) -7-oxo-7H-pyrido[1,2,3-de][1,4]benzoxazine-6-carboxylic acid hydrochloride hemihydrate.

Compounds (I) of this invention can be used as acid addition salts owing to the basic nature of the piperazinyl group of the 10-position. Examples of acid addition salts include inorganic salts such as hydrochloride, hydrobromide, hydroiodide, sulfate, etc. and organic salts such as acetate, methanesulfonate, citrate, benzenesulfonate, lactate, etc.

The carboxy group at the 6-position may take a salt form including alkali metal salts such as sodium salt, potassium salt, etc., alkaline earth metal salts such as magnesium salt, calcium salt, etc., ammonium salts, and organic salts such as triethylamine salt, etc.

Furthermore, salts of Compound (I) can be used in hydrate forms.

For the preparation of racemates of Compound (I) the methods described in Japanese Patent Laid-open Nos. 46986/1982 and 72589/1983, for example, can be used. The method described in Japanese Patent Laid-open No. 252790/1987 can be given as an example of the method for preparing 3S-type compounds.

Compounds (I), their salts or hydrates [hereinafter collectively referred to as Active Compounds (I)] can be administered to animals by oral administration, as is or mixed with feed. Alternatively, they can be dissolved in water and the solution is orally administered as is, mixed with feed, or further diluted with water. Injection is another method for administrating the Active Compounds (I).

The dose depends upon the purpose of the administration, e.g., prevention, cure, etc., kinds and body weight of animals to be treated, types of microorganisms causing the infection, the degree of infection, and the like. In general, 1-200 mg per day, preferably 5-100 mg per day, is dosed once or several times a day. These ranges are, however, an approximate standard, and it is possible to administer Active Compound (I) in an amount outside the above range, depending on the age, body weight, and degree of disease of the animal. There are no specific limitations as to the period during which Active Compound (I) is administered to animals. Usually, the administration for a period of 1-10 days gives a sufficient result. Intermittent administration is also possible.

Active Compound (I) can be dosed to animals in various forms of preparations that can be prepared according to conventional methods such as powders, subtilized granules, solubilizable powders, syrups, solutions, injections, and the like. Hereinafter are presented typical formulations comprising Active Compound (I).

| Components | Amount (parts by weight) |
|---|---|
| Formulation Example 1 | |
| Preparation for mixing with feed | |
| Active Compound (I) | 1-10 |
| Corn Starch | 98.5-89.5 |
| Light anhydrous silicic acid | 0.5 |
| Total | 100 |
| Formulation Example 2 | |
| Preparation for mixing with feed or water | |
| Active Compound (I) (Water Soluble) | 1-10 |
| Lactose | 90-99 |
| Total | 100 |
| Formulation Example 3 | |
| Liquid Preparation | |
| Active Compound (I) | 1-10 |
| Acetic acid or sodium hydroxide | 5-20 |
| Ethyl parabenzoate | 0.1 |
| Purified water | 69.9-93.9 |
| Total | 100 |

The antimicrobial agents of the present invention exhibit a wide spectrum of activity against various bacteria causing infectious diseases in animals. They exhibit strong activities against bacteria belonging to genera, for example, of Escherichia, Salmonella, Pasteurella, Haemophilus, Bordetella, Staphylococcus, Mycoplasma, etc. They are therefore useful for the prevention, cure, and treatment of infectious diseases of cattle, pigs, birds, dogs, cats, and the like. Named as specific infectious diseases against which the antimicrobial agent of this invention is effective are; for diseases of cattle, E. coli infection, Salmonella infection, Mycoplasma infection, hemorrhagic septicemia, bovine contiguous pleuropneumonia, mastitis, etc.; for diseases of pigs, E. coli infection, Salmonella infection, Pasteurella infection, Mycoplasma infection, atrophic rhinitis, exudative epidermitis, etc.; for diseases of birds, E. coli infection, chicken pullorum, paratyphoid, birds, cholera, infectious coryza, staphylococcus infection, Mycoplasma infection, etc.; for diseases of dogs, E. coli septicemia, Salmonella infection, hemorrhagic septicemia, eterus empyema, cystitis, etc.; and for diseases of cats, pleurisy, cystitis, Haemophilus infection, diarrhea, Mycoplasma infection, etc.

Among the compounds of this invention, Compound No. 6, 3S-9-fluoro-2,3dihydro-3-methyl-10-(4-ethyl-1-piperazinyl) -7-oxo-7H-pyrido[1,2,3-de][1,4]benzoxazine-6-carboxylic acid has especially excellent antimicrobial activity for various bacteria including gram positive microorganisms. In particular, the compound exhibits a high blood concentration when administered to animals. For example, in a test in which Compound No. 6 was orally administered to a dog at a dose of 10 mg/kg its blood concentration 1 hour after the administration was 6 μg/ml. This evidences an outstanding effect of this compound in animal bodies.

Other features of the invention will become apparent in the course of the following description of exemplary embodiments which are given for illustration of the invention and are not intended to be limiting thereof.

EXAMPLES

In the following examples, the Active Compounds listed in Table 1 below were prepared or used.

TABLE 1

Formula:

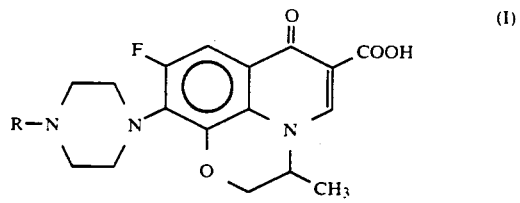

(I)

| Compound Nos. | R in formula (I) | Types |
|---|---|---|
| (1) | $CH_3-$ | 3S-type compound, Hemihydrate |
| (2) | $C_2H_5-$ | 3(RS), (Racemate) |
| (3) | $n-C_3H_7-$ | 3(RS), (Racemate) |
| (4) | $(CH_3)_2CH-$ | 3(RS), (Racemate) |
| (5) | $n-C_4H_9-$ | 3(RS), (Racemate) |
| (6) | $C_2H_5-$ | 3S-type compound |
| (7) | $n-C_3H_7-$ | 3S-type compound |
| (8) | $C_2H_5-$ | 3(RS), (Racemate) Hemihydrate hydrochloride |

EXAMPLE 1

Measurement of in vitro antimicrobial activity Active Compounds (I) against pathogenic bacteria derived from animals (Part 1):

The test microorganisms listed in Table 2 were cultured overnight in heart infusion broth (produced by Eiken Chemical Co., Ltd.). Culture broth containing about $10^8$/ml cells was diluted to a volume of 100 times. An aliquot (about 0.05 ml) of the diluted broth was inoculated onto a Mueller Hinton agar plate (produced by Eiken Chemical Co., Ltd.) to which Compound No. 1 was added in a prescribed concentration. After incubation at 37° C. for 18 to 24 hours, the minimum inhibitory concentration (MIC), i.e., the minimum concentration of Compound No. 1 inhibiting the growth of the inoculated cells, was determined. The results are shown in Table 2.

TABLE 2

In vitro Antimicrobial Activity Against Pathogenic Bacteria Derived From Animals (Part 1: Compound No. 1)

| Animals | Tested microorganisms | (MIC, μg/ml) Compound No. 1 | Control Compound* |
|---|---|---|---|
| Cow | Escherichia coli 15-4 | 0.05 | 0.1 |
| Pig | Escherichia coli 164 | 0.05 | 0.1 |
| Pig | Salmonella typhimurium 595 | 0.05 | 0.1 |
| Pig | Bordetella bronchiseptica AR3 | 0.2 | 0.39 |
| Chicken | Escherichia coli 442 | 0.025 | 0.05 |
| Chicken | Salmonella typhimurium 101 | 0.025 | 0.05 |
| Chicken | Staphylococcus aureus Aichi 2 | 0.1 | 0.2 |

*Ofloxacin (Japanese Patent Laid-Open No. 184014/1985).

Table 2 shows that Compound No. 1 of the present invention exhibits higher antimicrobial activities than its racemic isomer (Ofloxacin).

EXAMPLE 2

Measurement of in vitro antimicrobial activity of Active Compounds (I) against pathogenic bacteria derived from animals (Part 2):

The MIC of Compounds (1)-(8) against various pathogenic bacteria derived from animals was determined in the same manner as in Example 1. The results are shown in Table 3.

TABLE 3 in vitro antimicrobial activity against pathogenic bacteria derived from animals (Part 2: Compounds No. 1-8)

| | | (MIC, μg/ml) Compound | | | | | | | | Control |
|---|---|---|---|---|---|---|---|---|---|---|
| Animals | Tested microorganisms | No. 1 | No. 2 | No. 3 | No. 4 | No. 5 | No. 6 | No. 7 | No. 8 | Compound* |
| Cow | Escherichia coli 139 | 0.05 | 0.2 | 0.39 | 0.78 | 0.78 | 0.1 | 0.2 | 0.2 | 0.78 |
| Pig | Escherichia coli 881 | 0.05 | 0.1 | 0.2 | 0.39 | 0.78 | 0.1 | 0.2 | 0.2 | 0.39 |
| Pig | Salmonella typhimurium 569 | 0.05 | 0.1 | 0.39 | 0.78 | 0.78 | 0.1 | 0.2 | 0.2 | 0.39 |
| Pig | Bordetella bronchiseptica OKM-1 | 0.2 | 0.2 | 0.78 | 0.78 | 0.78 | 0.2 | 0.39 | 0.39 | 1.56 |
| Pig | Pasteurella multocida DB-12-1 | — | 0.05 | 0.1 | 0.2 | 0.1 | — | — | — | 0.2 |
| Chicken | Escherichia coli S6W | 0.025 | 0.1 | 0.39 | 0.78 | 0.78 | 0.1 | 0.2 | 0.2 | 0.39 |
| Chicken | Salmonella typhimurium 103 | 0.05 | 0.2 | 0.78 | 0.78 | 1.56 | 0.1 | 0.2 | 0.2 | 0.78 |
| Chicken | Staphylococcus aureus Yamaguchi 6 | 0.05 | 0.39 | 0.78 | 0.78 | 0.78 | 0.2 | 0.2 | 0.39 | 3.13 |

*Oxolinic acid

As evident from Table 3, Compound Nos. 1-8 of this invention exhibit higher in vitro antimicrobial activities than oxolinic acid, which is widely used as an antimicrobial agent for animals.

EXAMPLE 3

Measurement of in vitro antimicrobial activity of Active Compounds (I) against pathogenic bacteria derived from various animals (Part 3: Compounds No. 1, 2, and 6)

MIC of Compounds No. 1, 2, and 6 against various pathogenic bacteria derived from animals was determined in the same manner as in Example 1. The results are shown in Table 4.

TABLE 4

In Vitro Antimicrobial Activity Against Pathogenic Bacteria Derived From Animals (Part 3)

| | | (MIC, μg/ml) Compound | | | Control |
|---|---|---|---|---|---|
| Animals | Tested microorganisms | No. 1 | No. 2 | No. 6 | Compound* |
| Pig | Escherichia coli 164 | 0.05 | 0.1 | 0.1 | 0.1 |
| Pig | Escherichia coli 178 | 0.05 | 0.1 | 0.05 | 0.1 |
| Pig | Escherichia coli 191 | 0.05 | 0.1 | 0.05 | 0.1 |
| Cow | Escherichia coli 1-1 | 0.05 | 0.1 | 0.1 | 0.1 |
| Cow | Escherichia coli 7-5 | 0.05 | 0.1 | 0.05 | 0.1 |
| Cow | Escherichia coli 15-4 | 0.05 | 0.1 | 0.1 | 0.1 |
| Pig | Bordetella bronchiseptica AR-3 | 0.2 | 0.39 | 0.2 | 0.39 |
| Pig | Bordetella bronchiseptica BB-5 | 0.2 | 0.39 | 0.2 | 0.39 |
| Pig | Bordetella bronchiseptica BB-9 | 0.1 | 0.39 | 0.2 | 0.39 |
| Dog | Brucella canis | 0.78 | 1.56 | 0.20 | 0.78 |
| Dog | Yersinia pseudotuberculosis | 0.20 | 0.20 | 0.20 | 0.39 |
| Dog | Streptococcus faecalis | 0.78 | 3.13 | 1.56 | 3.13 |
| Dog | Lactobacillus casei | 0.78 | 0.78 | 0.78 | 1.56 |

*Ofloxacin

EXAMPLE 4

Antimicrobial activities of Active Compounds against *Mycoplasma gallisepticum* derived from chicken:

Various test strains of *Mycoplasma gallisepticum* derived from chicken were cultured in a Frey liquid medium for Mycoplasma for 3 days. The culture broth containing about $10^8$/ml cells was diluted to a volume of 100 times. The diluted broth was inoculated into Frey liquid media for Mycoplasma to which the compounds of the present invention were added at prescribed concentrations. The cells were incubated at 37° C. for 3 to 5 days while daily observing the color of the media. Among the culture broths maintaining red color at the time when the control to which no test compound was added turned yellow, the concentration of the broth having the minimum concentration was taken as the MIC of the compound. The results are shown in Table 5.

shown in Table 6 and demonstrate the superior effectiveness of Compound (1) against *Escherichia coli* infection of chicken.

TABLE 6

| Tested Compound | Concentration in feed (ppm) | No. of Tested chickens | No. of Dead chickens | Chickens developing disease in air sac (naked eye observation) | *Escherichia coli* collected in | | | Dose (mg/kg/day) |
|---|---|---|---|---|---|---|---|---|
| | | | | | Trachea ** | Lung ** | Air sac ** | |
| (1) | 50 | 5 | 0 | 0 | 0 | 0 | 0 | 8.4 |
| | 25 | 5 | 0 | 1 | 0 | 0 | 0 | 4.2 |
| | 12.5 | 5 | 1 | 3 | 2.78 | 2.78 | 3.99 | 2.0 |
| OFLX * | 50 | 5 | 1 | 2 | 0 | 0 | 0 | 7.9 |
| | 25 | 5 | 1 | 3 | 4.58 | 1.86 | 3.90 | 3.5 |
| | 12.5 | 5 | 2 | 3 | 7.48 | 5.26 | 4.20 | 1.6 |
| Control | 0 | 5 | 2 | 3 | 4.95 | 3.83 | 5.26 | — |

* Ofloxacin: Control compound
** Logarithmic number of collected cells per 1 g of tissue

TABLE 5

In Vitro Antimicrobical Activity Against *Mycoplasma gallisepticum* Derived From Chicken

| Tested microorganisms (*Mycoplasma gallisepticum*) | (MIC μg/ml) | | | | | Control Compound* |
|---|---|---|---|---|---|---|
| | Test Compound | | | | | |
| | No. 1 | No. 2 | No. 3 | No. 4 | No. 5 | |
| Strain 2004 | 0.0125 | 0.025 | 0.025 | 0.05 | 0.025 | >100 |
| Strain 2012 | 0.025 | 0.025 | 0.05 | 0.05 | 0.025 | >100 |
| Strain T-2 | 0.05 | 0.1 | 0.2 | 0.39 | 0.1 | >100 |
| Strain T-7 | 0.05 | 0.1 | 0.39 | 0.39 | 0.1 | NT** |
| Strain DP-1047 | 0.025 | 0.1 | 0.2 | 0.2 | 0.1 | >100 |

*Oxolinic acid
**Not tested

EXAMPLE 5

Effect of oral administration on chicken inoculated with *Escherichia coli*

*Escherichia coli* cells collected from infected chickens were cultured overnight in a trypticase soy broth (BBL). 0.2 ml of this culture broth was injected into the trachea of chickens of average body weight of 80 g using a 1 ml disposable injection needle. Beginning 2 hours after the inoculation, feeds to which Compound (1) had been added in the amount of 50 ppm, 25 ppm, or 12.5 ppm were freely given to the chickens for 5 days. Following the administration of Compound (1) the chickens were given feed with no addition of drug for 5 days. The surviving chickens were sacrificed and dissected. After examination of the degree of disease in the air sac, *Escherichia coli* in the trachea, lung, and air sac were quantitatively determined. The results are

EXAMPLE 6

Effect of oral administration on chickens inoculated with *Mycoplasma gallisepticum* (Part 1):

*Mycoplasma gallisepticum* cells collected from chickens having respiratory Mycoplasma infection were cultured for 3 days in a Frey liquid medium for Mycoplasma. 0.2 ml of this culture broth was injected into the trachea of chickens of an average body weight of 80 g using a 1 ml disposable injection needle. Beginning from the next day following the inoculation, feeds to which Compound (1) had been added in the amount of 100 ppm, 75 ppm, or 50 ppm were freely given to the chickens for 5 days. Following the administration of Compound (1) the chickens were given feed containing no drug for a further 5 days. The surviving chickens were sacrificed and dissected. After examination of the degree of disease in the air sac, *Mycoplasma gallisepticum* in the infraorbital sinus, trachea, lung, and air sac were determined. The results are shown in Table 7 and demonstrate the superior effectiveness of Compound (1) against *Mycoplasma gallisepticum* infection of chickens.

TABLE 7

| Tested Compound | Concentration in feed (ppm) | No. of tested chickens | No. of dead chickens | Chickens developing disease in air sac (naked eye observation) | *Mycoplasma gallisepticum* collected in | | | | Dose (mg/kg/day) |
|---|---|---|---|---|---|---|---|---|---|
| | | | | | Infraorbital sinus ** | *** Trachea | *** Lung | *** Air sac | |
| (1) | 100 | 5 | 0 | 0 | 0/5 | 0 | 0 | 0 | 14.9 |
| | 75 | 5 | 0 | 0 | 0/5 | 0 | 0 | 0 | 10.9 |
| | 50 | 5 | 0 | 0 | 0/5 | 0 | 0 | 2.32 | 7.7 |
| OFLX * | 100 | 5 | 0 | 0 | 0/5 | 0 | 0 | 0 | 16.1 |
| | 75 | 5 | 0 | 0 | 0/5 | 3.82 | 4.00 | 0 | 11.9 |
| | 50 | 5 | 0 | 1 | 1/5 | 3.64 | 4.78 | 3.70 | 8.3 |

TABLE 7-continued

Effect of administration on chicken inoculated with *Mycoplasma gallisepticum*

| Tested Compound | Concentration in feed (ppm) | No. of tested chickens | No. of dead chickens | Chickens developing disease in air sac (naked eye observation) | *Mycoplasma gallisepticum* collected in | | | | Dose (mg/kg/day) |
|---|---|---|---|---|---|---|---|---|---|
| | | | | | Infraorbital sinus ** | *** Trachea | *** Lung | *** Air sac | |
| Control | 0 | 5 | 0 | 2 | 4/5 | 4.36 | 4.62 | 5.81 | — |

\* Ofloxacin: Control compound
\*\* positive chicken/tested chicken
\*\*\* Logarithmic number of collected cells per 1 g of tissue

EXAMPLE 7

Effect of oral administration on chicken inoculated with *Mycoplasma gallisepticum* (Part 2):

The effects of oral administration of Compounds (2) and (3) on chickens inoculated with *Mycoplasma gallisepticum* were investigated the same way as in Example 5. The results are shown in Table 8 and demonstrate the superior effectiveness of compounds (2) and (3) against *Mycoplasma gallisepticum* infection of chickens.

-7-oxo-7H-pyrido[1,2,3-de][1,4]benzoxazine-6-carboxylic acid hydrochloride hemihydrate.

m.p. 285°–290° C. (decomposed).
Elemental analysis: for $C_{19}H_{22}O_4N_3F \cdot HCl \cdot 0.5H_2O$;
Calculated: C: 54.22 H: 5.75 N: 9.98 (%);
Found: C: 54.20 H: 5.79 N: 9.85 (%).

EXAMPLE FOR PREPARING COMPOUND (5)

1.5 g of anhydrous sodium carbonate was added to a mixture of 2.0 g of 3(RS)-9-fluoro-2,3-dihydro-3-methyl-10-(1-piperazinyl)-7-oxo-7H-pyrido[1,2,3-de][1,4-

TABLE 8

Effect of administration on chicken inoculated with *Mycoplasma gallisepticum*

| Tested Compound | Concentration in feed (ppm) | No. of tested chickens | No. of dead chickens | Chickens developing disease in air sac (naked eye observation) | *Mycoplasma gallisepticum* collected in | | | | Dose (mg/kg/day) |
|---|---|---|---|---|---|---|---|---|---|
| | | | | | Infraorbital sinus ** | *** Trachea | *** Lung | *** Air sac | |
| (2) | 100 | 5 | 0 | 0 | 0/5 | 0 | 0 | 0 | 16.1 |
| | 75 | 5 | 0 | 0 | 0/5 | 0 | 0 | 0 | 11.5 |
| | 50 | 5 | 0 | 0 | 0/5 | 2.96 | 2.43 | 2.08 | 8.1 |
| (3) | 100 | 5 | 0 | 0 | 0/5 | 0 | 0 | 0 | 15.0 |
| | 75 | 5 | 0 | 0 | 0/5 | 0 | 0 | 0 | 11.9 |
| | 50 | 5 | 0 | 0 | 0/5 | 0 | 2.38 | 3.24 | 8.1 |
| OFLX * | 100 | 5 | 0 | 0 | 0/5 | 0 | 0 | 0 | 16.1 |
| | 75 | 5 | 0 | 0 | 0/5 | 3.82 | 4.00 | 0 | 11.9 |
| | 50 | 5 | 0 | 1 | 1/5 | 3.64 | 4.78 | 3.70 | 8.3 |
| Control | — | 5 | 0 | 2 | 4/5 | 4.36 | 4.62 | 5.81 | — |

\* Ofloxacin: Control compound
\*\* Normal chicken/tested chicken
\*\*\* Logarithmic number of collected cells per 1 g of the tissue

EXAMPLE 8

Acute toxicity test:

Representative test compounds, Compounds (2) and (3), were intravenously injected into mice. No fatalities occurred at a dose of 200 mg/kg (10 mice/group), for Compound (2), and a dose of 200 mg/kg (6 mice/group), for Compound (3). From the results, the LD$_{50}$ values of the compounds are considered to be greater than 200 mg/kg.

SYNTHETIC EXAMPLES

Presented hereinbelow are examples for preparing Compounds (5), (8), and (7) used in the tests hereinabove.

EXAMPLE FOR PREPARING COMPOUND (8)

2.0 g of 3(RS)-9-fluoro-2,3-dihydro-3-methyl-10-(4-ethyl-1-piperazinyl)-7-oxo-7H-pyrido[1,2,3-de][1,4-]benzoxazine-6-carboxylic acid and 2.0 ml of concentrated hydrochloric acid were added to 50 ml of ethanol, and the mixture was heated to dissolution. Excess ethanol was evaporated under reduced pressure, and the deposited crystals were collected by filtration. Crystals were washed with ethanol and recrystallized from a water-ethanol solvent to produce 1.3 g of 3(RS)-9-fluoro-2,3-dihydro-3-methyl-10-(4-ethyl-1-piperazinyl)

]benzoxazine-6-carboxylic acid hydrate, 20 ml of dimethylformamide, and 10 ml of water, and the mixture was stirred at room temperature for 10 minutes. After the addition of 2.0 g of n-butylbromide, the mixture was further stirred at the same temperature for 1 hour. 1.0 g of n-butylbromide and 1.0 g of triethylamine were further added, and the stirring was continued at 60°–70° C. for 5.5 hours. After reaction, the resultant mixture was condensed and water added to the condensate. The aqueous solution was weakly acidified with hydrochloric acid with ice cooling, then made weakly basic (pH 8–9) with the addition of aqueous ammonia, and extracted with chloroform. The water layer was neutralized and again extracted with chloroform. The chloroform layers obtained by the two extractions were collected, washed with water, and dried over anhydrous sodium sulfate. After evaporation of the solvent, 5 ml of concentrated hydrochloric acid, 40 ml of tetrahydrofuran, and 20 ml of chloroform were added to the residue, and the mixture was stirred at 60°–70° C. for 4 hours. After reaction, the solvent was evaporated, and water was added to the residue. The aqueous solution was made weakly basic (pH 8–9), with the addition of aqueous ammonia, and extracted with chloroform. The water layer was neutralized with acetic acid and again extracted with chloroform. The chloroform layer obtained was mixed with the chloroform layer obtained in the initial extraction, washed with water, and dried over anhydrous sodium sulfate. After evaporation of the solvent, activated carbon was added to the residue and recrystallization was carried out in a chloroform-acetonitrile solvent. The crystals obtained were again recrystallized in a mixed solvent of concentrated ammonia, methanol, and water to produce 300 mg of 3(RS)-9-fluoro-2,3-dihydro-3-methyl-10-(4-n-butyl-1-piperazinyl) -7-oxo-7H-pyrido[1,2,3-de][1,4]benzoxazine-6-carboxylic acid.

m.p. 241°-244° C. (decomposed).
Elemental analysis: for $C_{21}H_{26}O_4N_3F$;
Calculated: C: 62.51 H: 6.50 N: 10.41 (%);
Found: C: 62.42 H: 6.56 N: 10.39 (%).

EXAMPLE FOR PREPARING COMPOUND (7)

To a suspension of 19.9 g of 3S-(-)-9,10-difluoro-2,3-dihydro-3-methyl-7-oxo-7H-pyrido[1,2,3-de][1,4]-benzoxazine-6-carboxylic acid borondifluoro chelate in 48 ml of dimethylsulfoxide was added dropwise a solution of 23.1 g of N-(n-propyl)piperazine in 8 ml of dimethylsulfoxide with ice-cooling and stirring. The mixture was stirred for 24 hours at room temperature. After completion of the reaction, 120 ml of water was added with ice-cooling and stirring to collect the deposited crystals by filtration. The crystals were washed with water to dryness to produce 21.3 g of yellow crystals. To the crystals were added 29.1 g of triethylamine, 200 ml of acetonitrile, and 200 ml of water, and the mixture refluxed for 6 hours with stirring. The resultant reaction mixture was condensed and dried, and the residue obtained was dissolved in chloroform, washed with water, and dried over anhydrous sodium sulfate. After evaporation of the solvent, the residue was repeatedly recrystallized from a mixed solvent of concentrated aqueous ammonia and ethanol to produce 10.1 g of 3S(-)-9-fluoro-2,3-dihydro-3-methyl-10-(4-n-propyl-1-piperazinyl) -7-oxo-7H-pyrido[1,2,3-de][1,4]-benzoxazine-6-carboxylic acid.

m.p. 219°-222° C. (decomposed).
Optical rotation:
$[\alpha]_D^{CHCL_3} = -112.43°$
c=0.201
l=10.0 (cm)
Elemental analysis: for $C_{20}H_{24}O_4N_3F$;
Calculated: C: 61.68 H: 6.21 N: 10.79 (%).
Found: C: 61.45 H: 6.35 N: 10.73 (%).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A pharmaceutical composition, comprising a pharmaceutically effective amount of 3S-9-fluoro-2,3-dihydro-3-methyl-10-(4-ethyl-1-piperazinyl)-7-oxo-7H-pyrido[1,2,3-de][1,4]benzoxazine-6-carboxylic acid in admixture with a pharmaceutically acceptable carrier.

2. A method for preventing or treating a disease in an animal comprising administering an effective amount of 3S-9-fluoro-2,3-dihydro-3-methyl-10-(4-ethyl-1-piperazinyl)-7-oxo-7H-pyrido [1,2,3-de][1,4]benzoxazine-6-carboxylic acid, wherein said disease is selected from the group consisting of bovine E. coli infection, bovine Salmonella infection, bovine Mycoplasma infection, bovine hemorrhagic septicemia, bovine contiguous pleuropneumonia, bovine mastitis, porcine E. coli infection, porcine Salmonella infection, porcine Pasteurella infection, porcine Mycoplasma infection, porcine atrophic rhinitis, porcine exudative epidermitis, avian E. coli infection, chicken pullorum, avian paratyphoid, avian cholera, avian infectious coryza, avian staphylococcus infection, avian Mycoplasma infection, canine E. coli septicemia, canine Salmonella infection, canine hemorrhagic septicemia, canine uterus empyema, canine cystitis, feline pleurisy, feline cystitis, feline Haemophilus infection, feline diarrhea, and feline Mycoplasma infection.

* * * * *